United States Patent
Ahmed et al.

(10) Patent No.: US 10,010,701 B2
(45) Date of Patent: Jul. 3, 2018

(54) LOCKING ASSEMBLY FOR A DRAINAGE CATHETER

(75) Inventors: Mahfuza Ahmed, Bloomington, IN (US); Kate Duncan, Mooresville, IN (US); James B. Hunt, Bloomington, IN (US); Bonita L. Nickless, Spencer, IN (US); Nancy L. Hutchinson, Spencer, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/944,840

(22) Filed: Nov. 12, 2010

(65) Prior Publication Data

US 2011/0125135 A1    May 26, 2011

Related U.S. Application Data

(60) Provisional application No. 61/264,060, filed on Nov. 24, 2009.

(51) Int. Cl.
*A61M 27/00* (2006.01)
*A61M 25/04* (2006.01)
(Continued)

(52) U.S. Cl.
CPC ......... *A61M 25/04* (2013.01); *A61M 25/0017* (2013.01); *A61M 27/00* (2013.01)

(58) Field of Classification Search
CPC ... A61M 25/0017; A61M 25/04; A61M 27/00
(Continued)

(56) References Cited

U.S. PATENT DOCUMENTS

| 4,643,720 A | 2/1987 | Lanciano |
| 4,740,195 A | 4/1988 | Lanciano |

(Continued)

FOREIGN PATENT DOCUMENTS

| EP | 00343910 | 6/1993 |
| WO | WO09207215 | 4/1992 |

(Continued)

OTHER PUBLICATIONS

International Search Report, issued in commonly owned PCT/US2010/052797, dated Dec. 8, 2010.
(Continued)

*Primary Examiner* — Tatyana Zalukaeva
*Assistant Examiner* — Andrew J Mensh
(74) *Attorney, Agent, or Firm* — Brinks Gilson & Lione

(57) ABSTRACT

A drainage catheter includes an elongated tubular member and a locking assembly. The locking assembly includes a first protruding element and a collar. The first protruding element is disposed proximal to a port in the tubular member through which a proximal portion of a tension member may exit. The collar is coaxially disposed about the tubular member and has a second protruding element projecting from an interior surface of the collar. The collar is configured for longitudinal sliding movement relative to the tubular member such that the collar may be moved along the tubular member toward the proximal end of the tubular member thereby interacting with the first protruding element and securing the proximal portion of the tension member between the first protruding element and the collar.

9 Claims, 2 Drawing Sheets

(51) Int. Cl.
  *A61M 1/00* (2006.01)
  *A61M 5/32* (2006.01)
  *A61M 25/00* (2006.01)
(58) Field of Classification Search
  USPC .................................. 604/544, 543, 175, 540
  See application file for complete search history.

(56) References Cited

U.S. PATENT DOCUMENTS

| | | | |
|---|---|---|---|
| 4,825,859 A * | 5/1989 | Lambert .................. 128/202.16 |
| 5,399,165 A | 3/1995 | Paul, Jr. |
| 5,489,269 A | 2/1996 | Aldrich et al. |
| 5,551,147 A * | 9/1996 | Morse et al. ................... 29/764 |
| 5,637,102 A | 6/1997 | Tolkoff et al. |
| 5,989,241 A | 11/1999 | Plishka et al. |
| 6,159,177 A | 12/2000 | Amos, Jr. et al. |
| 6,299,598 B1 | 10/2001 | Bander |
| 6,454,740 B1 | 9/2002 | Mody |
| 6,508,789 B1 | 1/2003 | Sinnott et al. |
| 6,666,853 B2 | 12/2003 | Chu et al. |
| 6,699,233 B2 | 3/2004 | Slanda et al. |
| 6,743,198 B1 | 6/2004 | Tihon |
| 6,971,390 B1 | 12/2005 | Vasek et al. |
| 7,087,038 B2 | 8/2006 | Lee |
| 7,217,256 B2 | 5/2007 | Di Palma |
| 2001/0049490 A1 | 12/2001 | Slanda et al. |
| 2002/0091303 A1 | 7/2002 | Ootawara et al. |
| 2003/0230894 A1* | 12/2003 | Cleveland et al. ........... 285/239 |
| 2004/0039339 A1 | 2/2004 | Magnusson |
| 2005/0107739 A1* | 5/2005 | Palma .......................... 604/104 |
| 2006/0142695 A1 | 6/2006 | Knudson |
| 2006/0200079 A1* | 9/2006 | Magnusson ................. 604/164.1 |
| 2006/0212023 A1 | 9/2006 | Cross |
| 2006/0217667 A1 | 9/2006 | Accisano, III et al. |
| 2006/0264911 A1 | 11/2006 | Nelson et al. |
| 2007/0032779 A1 | 2/2007 | Accisano, III et al. |
| 2007/0049907 A1 | 3/2007 | Fischer, Jr. et al. |
| 2007/0078385 A1 | 4/2007 | Accisano, III et al. |
| 2007/0083189 A1 | 4/2007 | Lampropoulos et al. |
| 2007/0203474 A1 | 8/2007 | Ryan |
| 2008/0125756 A1* | 5/2008 | Dicarlo et al. ............... 604/543 |
| 2008/0200839 A1 | 8/2008 | Bunch et al. |
| 2008/0242932 A1 | 10/2008 | Carter |
| 2008/0312599 A1* | 12/2008 | Rosenberg .................... 604/175 |
| 2009/0171295 A1 | 7/2009 | Porter et al. |
| 2011/0054447 A1* | 3/2011 | Johnson et al. .............. 604/540 |

FOREIGN PATENT DOCUMENTS

| | | |
|---|---|---|
| WO | WO 94/07558 | 4/1994 |
| WO | WO 99/11315 | 3/1999 |

OTHER PUBLICATIONS

International Search Report, issued in PCT/US2010/056437, dated Jan. 14, 2011.

Supplementary European Search Report, issued in EP 10833770, filed Nov. 12, 2010, search completed Mar. 14, 2013.

\* cited by examiner

LOCKING ASSEMBLY FOR A DRAINAGE CATHETER

RELATED APPLICATIONS

This application claims the benefit of U.S. Provisional Application No. 61/264,060, filed Nov. 24, 2009, the entire content of which is hereby incorporated by reference herein.

TECHNICAL FIELD

This invention relates to drainage catheters and particularly to a locking mechanism for a drainage catheter for drawing and maintaining the distal end of the catheter into a desired configuration.

BACKGROUND

Suprapubic catheterization of the bladder is used to drain the bladder after surgery or when the genitourinary system is plugged by an obstruction. Other percutaneously inserted catheters are also used to drain the kidney or biliary system as well as to drain abscesses, other sites of fluid collection, and other viscera. Still other percutaneously inserted catheters are gastrostomy feeding tubes.

These catheters are typically introduced into the patient by means of a large hypodermic needle or trocar, which pierces the abdominal wall. A wire guide is inserted through the needle and then removed. The catheter tube with a stiffening cannula positioned therein is then passed over the wire guide into the cavity. The cannula and wire guide are withdrawn, leaving the catheter in the desired cavity. With respect to the bladder, the advantage of this technique is that irrigation and infection of the urinary tract is minimized. However, one problem with these catheters is that the catheter can be easily pulled out by movement of the body or by the emptying of, for example, the bladder. Another problem is that the distal end of the catheter, including the side ports therein, may be inadvertently drawn into the abdominal cavity, creating the potential for severe infections.

Various catheters have been developed with so-called pigtail loops at their distal ends for ensuring drainage of the cavity and preventing accidental removal therefrom. The pigtail loop is tightened by pulling on the proximal end of a flexible tension member, which extends through the catheter. The proximal end of this tension member is held in place by any one of a number of retention means. One known locking drainage catheter includes a lockable connector positioned about the proximal end of the catheter. The catheter also includes a flexible tension member that extends through the lockable connector for drawing the distal end of the catheter into a loop. The lockable connector includes a resilient material sleeve with a sleeve passage extending longitudinally therethrough for positioning the tension member therein. The sleeve is positioned in a passage of the connector adjacent a channel, wherein a pivotably attached lever is positioned. When the lever is pivoted toward the connector into a fixed position, a cam surface of the lever compresses the sleeve and locks thereabout to maintain the loop formed in the distal member end. Although the locking drainage catheter is well-suited for its intended purpose, the lockable connector portion of the catheter is somewhat bulky, which may make the device somewhat uncomfortable for a patient and which prevents the device from being used with relatively smaller sized access sheaths, e.g., 30 French access sheath.

It is desirable to provide a locking mechanism for use with a catheter, such as a drainage catheter, that overcomes the disadvantages present with available catheters and locking mechanisms.

BRIEF SUMMARY

In an aspect of the invention, a locking assembly for use with a tension member in a drainage catheter includes a first protruding element at a proximal end of the catheter, wherein the first protruding element is disposed proximal to a port in the catheter through which a proximal portion of the tension member may exit; a collar coaxially disposed about the catheter, the collar having a second protruding element projecting from an interior surface of the collar, wherein when the locking assembly is in an open position, the collar is disposed distal to the first protruding element and when the locking assembly is in a locked position, the second protruding element is disposed proximal to the first protruding element such that the proximal portion of the tension member is secured between the first protruding element and the second protruding element.

In a feature of this aspect, the locking assembly is dimensioned to fit within a 30 Fr access sheath. In another feature of this aspect, the first protruding element is disposed completely around the circumference of the catheter. In an additional feature of this aspect, the first protruding element is fixed to the catheter. In a further feature, the second protruding element is disposed completely around the circumference of the interior surface of the collar.

In another feature of this aspect, the collar further comprises a proximal portion and a tapered distal portion. With regard to this feature, the second protruding element extends from an interior surface of the proximal portion of the collar. In yet another feature, the first and second protruding elements are O-rings. With regard to this feature, the O-rings may comprise butadiene or butyl rubber.

In another aspect of the invention, a locking assembly for use with a tension member in a drainage catheter includes a first protruding element at a proximal end of the catheter, wherein the first protruding element is disposed proximal to a port in the catheter through which a proximal portion of the tension member may exit and a collar coaxially disposed about the catheter. The collar has a second protruding element projecting from an interior surface of the collar. The collar is configured for longitudinal sliding movement relative to the catheter such that the collar may be moved along the catheter toward the proximal end of the catheter thereby interacting with the first protruding element and securing the proximal portion of the tension member between the first protruding element and the collar.

In yet another aspect of the invention, a drainage catheter includes an elongated tubular member and a locking assembly. The tubular member has a distal end for insertion into a patient, a proximal end, and a passageway extending longitudinally therethrough. The distal end is formed to be positioned into a desired configuration. The locking assembly is engaged with the proximal end of the tubular member and comprises a first protruding element and a collar. The first protruding element is disposed proximal to a port in the tubular member through which a proximal portion of a tension member may exit. The collar is coaxially disposed about the tubular member and has a second protruding element projecting from an interior surface thereof. The collar is configured for longitudinal sliding movement relative to the tubular member such that the collar may be moved along the tubular member toward the proximal end of the tubular member thereby interacting with the first protruding element and securing the proximal portion of the tension member between the first protruding element and the collar.

DETAILED DESCRIPTION

Figure 1:
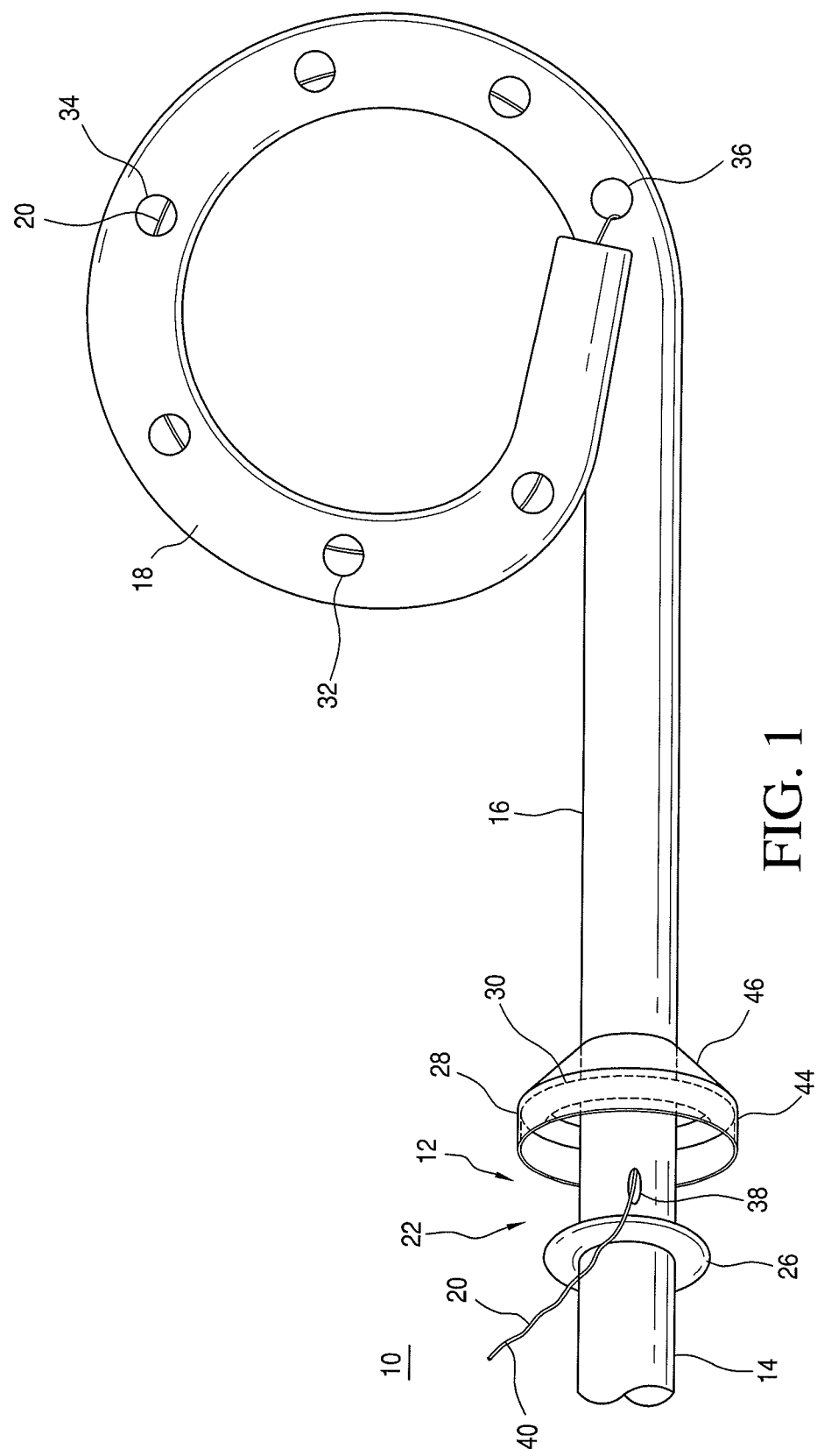
FIG. 1 is a side perspective view of a drainage catheter in accordance with an embodiment of the present invention in an open position.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated apparatus, and such further applications of the principles of the invention as illustrated therein being contemplated as would normally occur to one skilled in the art to which the invention relates.

In the following discussion, the terms "proximal" and "distal" will be used to describe the opposing ends of the drainage catheter, as well the opposing ends of component features of the catheter, such as the locking assembly. The term "proximal" is used in its conventional sense to refer to the end of the catheter or component feature that is closest to the operator during use. The term "distal" is used in its conventional sense to refer to the end of the catheter or component feature that is initially inserted into the patient or that is closest to the patient during use.

In one aspect, the present invention relates to a catheter, such as a drainage catheter 10, having a locking assembly 12 disposed at a proximal end 14 of the catheter 10. The catheter has a tubular member 16, the distal end 18 of which is lockable into a desired configuration, such as a loop or a pigtail, for retaining the catheter 10 in a body cavity, such as the bladder. A flexible tension member 20, such as a suture, extends through the locking assembly 12 and to the distal end 18 of the tubular member 16 for use in drawing the distal end 18 into the desired configuration, whereupon the locking assembly 12 is activated to maintain this configuration.

Figure 2:
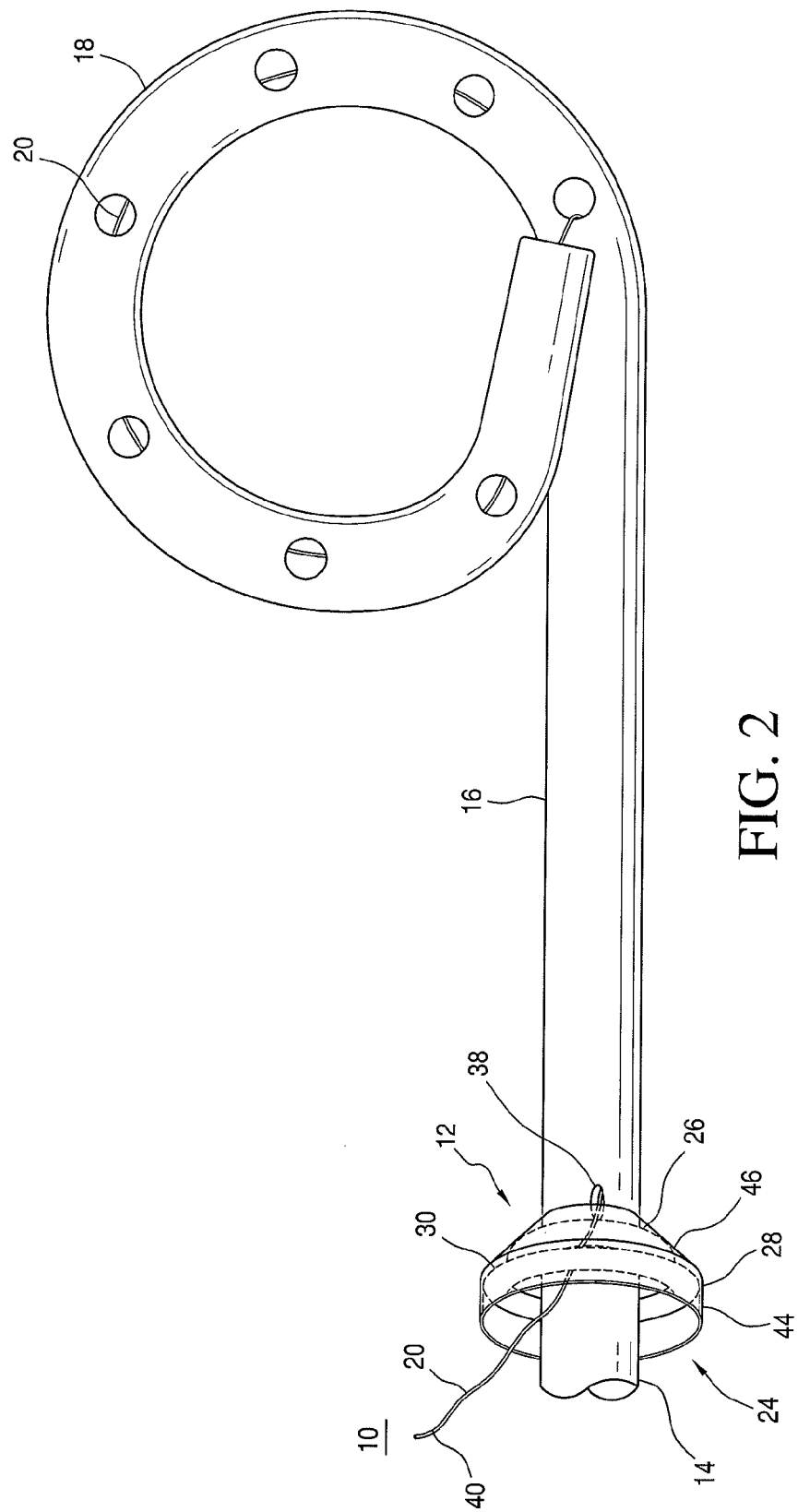
FIG. 2 is a side perspective view of a drainage catheter in accordance with an embodiment of the present invention in a locked position.

FIGS. 1 and 2 are representations of a drainage catheter 10 in accordance with an embodiment of the present invention. As illustrated, the drainage catheter 10 includes a locking assembly 12 positioned at the proximal end 14 of the catheter 10, and an elongated tubular member 16 extending in a distal direction from the locking assembly 12. In an exemplary embodiment, the tubular member 16 tapers to an open distal tip. As shown in FIG. 1, the locking assembly 12 is in the open position 22. As shown in FIG. 2, the locking assembly 12 is in the locked position 24, whereupon the distal end 18 of the tubular member 16 is locked into the desired configuration, in this case a loop. Locking the distal end 18 of the tubular member 16 into the desired configuration, e.g., a loop or a pigtail, inhibits unintended withdrawal or displacement of the catheter 10 from its position in the desired body cavity, e.g. the bladder of a patient.

In the embodiment shown, the locking assembly 12 comprises a first protruding element 26, a collar 28, and a second protruding element 30. The tubular member 16 has a passageway extending longitudinally between the distal end 18 and the locking assembly 12. A plurality of drainage ports 32, 34, 36 communicating with the passageway are positioned proximate the distal end 18 for receiving fluid to be drained from the body cavity. The tubular member 16 further includes an additional port 38 positioned proximate the drainage ports 32, 34, 36 and the distal end 18 and communicating with the passageway. A tension member 20, such as a suture, extends along the passageway, out through a tip of the tubular member 16, and back through one of the ports 32, 34, 36. The ports 32, 36 are spaced apart a predetermined length equal to the circumference of, e.g., the desired loop configuration.

The tension member 20 includes a proximal portion 40 that extends through the port 38 in the tubular member 16 for grasping and drawing the tension member 20 to form and hold the desired loop configuration at the distal end 18 of the tubular member 16. The tension member 20 further includes a distal portion (not shown), which may be fixedly attached to a component near the proximal end 14 of the catheter 10.

The first protruding element 26 is disposed at the proximal end 14 of the catheter 10, proximate the port 38 through which the tension member 20 exits for tensioning the tubular member 16. The first protruding element 26 may be fixed to the catheter 10, and it may extend around the entire circumference of the tubular member 16. Alternatively, the first protruding element 26 may extend around a portion of the circumference of the tubular member 16. The first protruding element 26 may be an O-ring, and it may be constructed of synthetic rubber (e.g., butadiene or butyl).

The collar 28 is coaxially disposed about the tubular member 16. The collar 28 has a proximal portion 44 from which the second protruding element 30 projects and a tapered distal portion 46. In particular, the second protruding element 30 projects from an interior surface of the proximal portion 44. In embodiments, the diameter of the second protruding element 30 may be larger than the diameter of the first protruding element 26. The larger diameter of the second protruding element 30, in turn, results in the diameter of the proximal portion 44 of the collar 28 being correspondingly large enough to accommodate the diameter of the second protruding element 30. As such, the whole of the proximal portion 44 of the collar 28 and the second protruding element 30 may not be in contact with the tubular member 16. The tapering of the distal portion 46 enables the collar 28 to remain relatively stable on the tubular member 16 despite the larger diameter of the proximal portion 44. As with the first protruding element 26, the second protruding element 30 may be an O-ring, and it may be constructed of synthetic rubber (e.g., butadiene or butyl). The locking assembly 12 may be manufactured in a CNC-lathe machine.

The collar 28 is configured for sliding movement along the length of the tubular member 16 with a relatively small amount of force. The collar 28 generally remains relatively close to the first protruding element 26 even in the open position 22. While the tapered profile of the distal portion 46 in the exemplary embodiment aids in maintaining relative positioning of the collar 28, one of ordinary skill in the art will understand that various configurations and adaptations may be used to maintain relative positioning of the collar 28.

When the locking assembly 12 is in the open position 22, the collar 28 is disposed distal to the first protruding element 26 and the tension member port 38. When the locking assembly 12 is in the locked position 24, the second protruding element 30 is disposed proximal to the first protruding element 26 and the tension member 20 is secured between the first protruding element 26 and the second protruding element 30.

In order to move the locking assembly 12 from the open position 22 to the locked position 24, the collar 28 is moved longitudinally along the tubular member 16 in a direction toward the first protruding element 26. The collar 28, including the second protruding element 30, interacts with the first protruding element 26 and the tension member 20 by sliding over the tension member port 38 and then over the first protruding element 26. The larger diameter of the second protruding element 30 aids in allowing the second protruding element 30 to slide over the first protruding element 26. When the locking assembly 12 is in the locked position 24, the first protruding element 26 is generally disposed between the second protruding element 30 and the tapered distal portion 46 of the collar 28. The tapered distal portion 46 aids in stabilizing the collar 28 in the locked position 24. A sealing relationship is formed between the first protruding element 26 and the second protruding element 30 such that the proximal portion 40 of the tension member 20 is secured between the first protruding element 26 and the second protruding element 30 thereby maintaining the configuration of the distal end 18 of the tubular member 16. To release the distal end 18 of the tubular member 16, pressure may be exerted on the collar 28 to move it toward the distal end 18 of tubular member 16. Once the second protruding element 30 is no longer in contact with the first protruding element 26, the seal between the two elements should be released thereby releasing the tension member 20.

A method of using the drainage catheter 10 with the locking assembly 12 will now be described. Initially, the distal end 18 of the tubular member 16 is percutaneously inserted into a body cavity, such as the bladder. This step is typically performed by inserting the distal end of a thin-walled hollow needle through the abdominal wall and into the bladder in a well-known manner. A wire guide is then inserted through the needle into the bladder, and the needle is removed, leaving the wire guide in place. A dilator may be used alone or in conjunction with an introducer or access sheath over the wire guide to increase the size of the puncture site. Existing locking assemblies or mechanisms are often large and bulky and hence not able to be used with introducers that are 30 French or smaller without deforming the introducer in some way. Advantageously, the locking assembly 12 is small enough that it may be used with 30 French introducers without deformation to the introducer.

During percutaneous insertion of the tubular member 16 over the wire guide, the catheter 10 will typically be manipulated into a generally straight configuration, with the locking assembly 12 in the open position as shown in FIG. 1. This generally straight configuration may be achieved by inserting a flexible stiffener (not shown) through the passageway of the elongated tubular member 16. Following insertion of the straightened distal end 18 of the tubular member 16 into the bladder, the wire guide and flexible stiffener are removed from the patient. The distal end 18 of the tubular member 16 is left in place for providing fluid flow from the bladder through the ports 32, 34, 36 and the distal tip to a conventional fluid collection system (not shown), such as a proximally extending piece of tubing and a plastic collection bag.

In order to inhibit unintended withdrawal or dislodgement of the distal end 18 of the tubular member 16 from the bladder, the locking assembly 12 is activated to achieve the desired distal end configuration, such as the loop shown in FIG. 2.

To achieve this configuration, the operator grasps and pulls on the proximal portion 40 of the tension member 20, while the locking assembly 12 is still in the unlocked, or open, position (FIG. 1). As the tension member proximal portion 40 is pulled, the tension member 20 is moved or drawn proximally to form the distal end 18 of the tubular member 16 into the desired loop configuration. In order to maintain the distal end 18 of the tubular member 16 in the desired loop configuration, the collar 28 is moved toward the proximal end 14 of the catheter 10 until the collar 28 slides over the first element 26 into the locked position 24 whereby the first protruding element 26 is disposed between the second protruding element 30 and the tapered portion 46 of the collar 28 in abutting relation with the second protruding element 30. The tension member 20 is secured between the first and the second protruding elements 26, 30, respectively. As a result, further pulling or other movement of the tension member 20 is substantially prevented, thereby maintaining the tension that forms the loop.

Those skilled in the art will recognize that not every feature of the catheter will be required in every instance, nor will every operating step described be required in every instance of use. Routine modifications may be made to the structure and the method of use from time to time, with all of the foregoing being considered to be within the scope of the invention. Those skilled in the art will appreciate that the various components of the catheter and locking assembly described herein may be fabricated from many possible materials that are suitable for such use, using standard techniques. Typically, various medical grade polymeric materials are desirable. For example, the collar may be formed from polyurethane, polypropylene, polyethylene, nylon, polyethylene terephthalate, polyethen, and any other suitable polymer and/or combinations thereof. Alternatively, the collar may be constructed of metal or a combination of metal and polymeric materials. Flexible tubular members suitable for use herein are well known in the art. The tubular member may be formed from any well-known material or combination of well-known materials, such as, for example, polyurethane.

It is to be understood that the above-described drainage catheter is merely an illustrative embodiment of the principles of this invention and that other connectors, catheters, and drainage apparatus may be devised by those skilled in the art without departing from the spirit and scope of this invention. In particular, the distal end of the catheter may be preformed into any desired configuration for positioning and retaining the distal end of the catheter in any part of a patient's body. It is further contemplated that the flexible tension member may be attached in any one of a number of well-known ways to the tubular member and drawable through one or more ports in the tubular member for positioning the distal end in the desired position. It is also further contemplated that the medical device of the present invention has application as an abscess or biliary drainage catheter, a nephrostomy tube in the renal pelvis, a gastrostomy feeding tube, or any other catheter requiring a distally positioned retention means such as a pigtail or loop.

We claim:

1. A locking assembly for use with a tension member in a drainage catheter, comprising:
   (a) a first protruding element fixedly positioned at a proximal end of the drainage catheter, wherein the first protruding element is disposed proximal to a port in the drainage catheter through which a proximal portion of the tension member may exit and wherein the first protruding element is disposed completely around a circumference of the drainage catheter;

(b) a collar coaxially disposed about the drainage catheter, the collar having a proximal portion, a tapered distal portion, and a second protruding element projecting from an interior surface of the collar, wherein when the locking assembly is in an open position, the collar is disposed distal to the first protruding element and when the locking assembly is in a locked position, the second protruding element is disposed proximal to the first protruding element such that the proximal portion of the tension member is secured by the first protruding element and the second protruding element in an abutting relation and the first protruding element is disposed between the second protruding element and the tapered distal portion within the interior surface of the collar, and wherein the diameter of the second protruding element is larger than the diameter of the first protruding element, wherein the first and second protruding elements are O-rings and wherein the second protruding element is not in contact with the tubular member.

2. The locking assembly of claim 1, wherein the locking assembly is dimensioned to fit within a 30 Fr access sheath.

3. The locking assembly of claim 1, wherein the second protruding element extends from an interior surface of the proximal portion of the collar.

4. The locking assembly of claim 1, wherein the O-rings comprise butadiene.

5. The locking assembly of claim 1, wherein the O-rings comprise butyl rubber.

6. A locking assembly for use with a tension member in a drainage catheter, comprising:
(a) a first protruding element fixedly positioned at a proximal end of the drainage catheter, wherein the first protruding element is disposed proximal to a port in the drainage catheter through which a proximal portion of the tension member may exit and wherein the first protruding element is disposed completely around a circumference of the drainage catheter;
(b) a collar coaxially disposed about the drainage catheter, the collar having a proximal portion, a tapered distal portion, and a second protruding element projecting from an interior surface of the collar, wherein the collar is configured for longitudinal sliding movement relative to the catheter such that the collar may be moved along the drainage catheter toward the proximal end of the drainage catheter thereby interacting with the first protruding element and the proximal portion of the tension member is secured by the first protruding element and the second protruding element in an abutting relation and wherein the first protruding element is disposed between the second protruding element and the tapered distal portion within the interior surface of the collar and wherein the diameter of the second protruding element is larger than the diameter of the first protruding element, wherein the first and second protruding elements are O-rings and wherein the second protruding element is not in contact with the tubular member.

7. A drainage catheter comprising
(a) an elongated tubular member, the tubular member having a distal end for insertion into a patient, a proximal end, and a passageway extending longitudinally therethrough, the distal end being formed to be positioned into a desired configuration;
(b) a locking assembly engaged with the proximal end of the tubular member, the locking assembly comprising a first protruding element fixedly positioned upon the tubular member and a collar;
(c) the first protruding element being disposed proximal to a port in the tubular member through which a proximal portion of a tension member may exit and wherein the first protruding element is disposed completely around a circumference of the drainage catheter;
(d) the collar being coaxially disposed about the tubular member and having a proximal portion, a tapered distal portion, and a second protruding element projecting from an interior surface of the collar, wherein the collar is configured for longitudinal sliding movement relative to the tubular member such that the collar may be moved along the tubular member toward the proximal end of the tubular member thereby interacting with the first protruding element and the proximal portion of the tension member is secured by the first protruding element and the second protruding element in an abutting relation wherein the first protruding element is disposed between the second protruding element and the tapered distal portion within the interior surface of the collar and wherein the diameter of the second protruding element is larger than the diameter of the first protruding element, wherein the first and second protruding elements are O-rings and wherein the second protruding element is not in contact with the tubular member.

8. The drainage catheter of claim 7, wherein the locking assembly is dimensioned to fit within a 30 Fr access sheath.

9. The drainage catheter of claim 7, wherein the second protruding element extends from an interior surface of the proximal portion of the collar.

* * * * *